US012773197B2

(12) United States Patent
Harp et al.

(10) Patent No.: US 12,773,197 B2
(45) Date of Patent: Oct. 27, 2026

(54) EXPANDABLE SPACEMAKER AND RELATED METHODS

(71) Applicant: AtriCure, Inc., Mason, OH (US)

(72) Inventors: Adam Harp, Cincinnati, OH (US); Jacob Luisi, Cincinnati, OH (US); Matthew Monti, Cincinnati, OH (US); Salvatore Privitera, Mason, OH (US); John Wesley, Annapolis, MD (US)

(73) Assignee: AtriCure, Inc., Mason, OH (US)

( * ) Notice: Subject to any disclaimer, the term of this patent is extended or adjusted under 35 U.S.C. 154(b) by 269 days.

(21) Appl. No.: 18/681,380

(22) PCT Filed: Aug. 9, 2022

(86) PCT No.: PCT/US2022/074679
§ 371 (c)(1),
(2) Date: Feb. 5, 2024

(87) PCT Pub. No.: WO2023/019115
PCT Pub. Date: Feb. 16, 2023

(65) Prior Publication Data

US 2024/0341742 A1 Oct. 17, 2024

Related U.S. Application Data

(60) Provisional application No. 63/231,292, filed on Aug. 10, 2021.

(51) Int. Cl.

| | |
|---|---|
| ***A61B 17/02*** | (2006.01) |
| ***A61B 1/32*** | (2006.01) |
| *A61B 17/00* | (2006.01) |

(52) U.S. Cl.
CPC ............ *A61B 17/0218* (2013.01); *A61B 1/32* (2013.01); *A61B 2017/00557* (2013.01); (Continued)

(58) Field of Classification Search
CPC ................................................. A61B 17/0237
See application file for complete search history.

(56) References Cited

U.S. PATENT DOCUMENTS 5,562,603 A * 10/1996 Moll ..................... A61B 90/50 600/207
2008/0306333 A1 12/2008 Chin
(Continued)

FOREIGN PATENT DOCUMENTS

EP 2 156 793 2/2010
WO PCT/US2022/074679 11/2022

*Primary Examiner* — Tessa M Matthews
(74) *Attorney, Agent, or Firm* — Dorton & Willis LLP; Ryan Willis

(57) ABSTRACT

Surgical instruments and devices for creating surgical working spaces and related methods are disclosed. An example surgical spacemaking device may include surgical spacemaking device an elongated connecting portion and an expandable spacemaking portion disposed distally on the connecting portion. The spacemaking portion may include an expandable lateral base portion, an expandable first vertical lateral portion configured to extend generally orthogonally from the lateral base portion, and an expandable second vertical lateral portion configured to extend generally orthogonally from the lateral base portion.

19 Claims, 11 Drawing Sheets

(52) U.S. Cl.
CPC ............... *A61B 2017/00862* (2013.01); *A61B 2017/0225* (2013.01); *A61B 2017/0237* (2013.01)

(56) References Cited

U.S. PATENT DOCUMENTS

| | | | | |
|---|---|---|---|---|
| 2009/0149716 | A1 | 6/2009 | Diao et al. | |
| 2009/0287046 | A1 | 11/2009 | Yamatani | |
| 2016/0242751 | A1 | 8/2016 | Bonadio et al. | |
| 2017/0172775 | A1* | 6/2017 | O'Neill ............ | A61B 17/12136 |
| 2020/0178764 | A1 | 6/2020 | Ibrahim et al. | |
| 2022/0287701 | A1* | 9/2022 | Borut ................. | A61B 17/0206 |

* cited by examiner

EXPANDABLE SPACEMAKER AND RELATED METHODS

CROSS REFERENCE TO RELATED APPLICATIONS

This application claims the benefit of U.S. Provisional Application No. 63/231,292, filed Aug. 10, 2021, which is incorporated by reference.

INTRODUCTION

The present disclosure is directed to surgical instruments and devices for creating surgical working spaces and related methods, and, more specifically, to expandable spacemaking devices and related methods.

The present disclosure contemplates that some surgical operations may involve procedures performed in potential spaces. As used herein, "potential space" may refer to a space between two adjacent anatomical structures that are normally pressed together, such as in a directly apposed manner. Generally, the adjacent anatomical structures of a potential space may be readily separated to create a realized space therebetween.

The present disclosure contemplates separating anatomical structures forming a potential space may be used to facilitate surgical procedures. Surgical devices utilized to separate anatomical structures, such as those forming a potential space, may be referred to as spacemaking devices.

While known spacemaking devices have been used safely and effectively to create surgical working spaces, improvements in the construction and operation of surgical spacemaking devices may be beneficial for users (e.g., surgeons) and patients. The present disclosure includes various improvements which may enhance the construction, operation, and methods of use of surgical spacemaking devices.

It is an aspect of the present disclosure to provide a surgical spacemaking device, including an elongated connecting portion and/or an expandable spacemaking portion disposed distally on the connecting portion and configured to create a working space. The spacemaking portion may include an expandable lateral base portion, an expandable first vertical lateral portion configured to extend generally orthogonally from the lateral base portion, and/or an expandable second vertical lateral portion configured to extend generally orthogonally from the lateral base portion.

In a detailed embodiment, when expanded, the lateral base portion, the first vertical lateral portion, and the second vertical lateral portion may generally form a C-shape.

In a detailed embodiment, the device may further include one or more tension elements. The one or more tension elements may be operatively coupled between the first vertical lateral portion and the second vertical lateral portion. The one or more tension elements may include a distal lateral tension element extending generally laterally between distal aspects of the first vertical lateral portion and the second vertical lateral portion. The one or more tension elements may include a proximal lateral tension element extending generally laterally between proximal aspects of the first vertical lateral portion and the second vertical lateral portion. The one or more tension elements may be generally elastic. The one or more tension elements may be generally inelastic.

In a detailed embodiment, the lateral base portion may include at least one lateral inflatable element.

In a detailed embodiment, the first vertical lateral portion may include at least one first longitudinal inflatable element and/or the second vertical lateral portion may include at least one second longitudinal inflatable element.

In a detailed embodiment, the lateral base portion and the first vertical lateral portion may be interposed by a first fold line and/or the lateral base portion and the second vertical lateral portion may be interposed by a second fold line.

In a detailed embodiment, the connecting portion may include at least one tether operatively coupled to the spacemaking portion. The at least one tether may be configured to fluidically couple at least one of the one or more inflatable elements to an external source of inflation fluid.

In a detailed embodiment, the connecting portion may include a sheath. The at least one tether may extend through the sheath. The sheath may be configured to receive an endoscope and/or an ablation device therethrough.

It is an aspect of the present disclosure to provide a method of creating a surgical working space, including advancing a spacemaking device to a surgical site proximate a target tissue and/or expanding a spacemaking portion of the spacemaking device to create a working space. Expanding the spacemaking portion may include inflating at least one lateral inflatable element and at least two longitudinal inflatable elements. The at least two longitudinal inflatable elements may be operatively coupled by at least one generally laterally oriented tension element.

In a detailed embodiment, expanding the spacemaking portion may include expanding the spacemaking portion to generally form a C-shape with the working space at least partially therein.

In a detailed embodiment, the spacemaking device may include a sheath. The method may include, before expanding the spacemaking portion, distally unsheathing the spacemaking portion from the sheath. The method may include advancing an endoscope and/or an ablation instrument through the sheath to the working space.

In a detailed embodiment, expanding the spacemaking portion may include sequentially inflating the at least one lateral inflatable element and the at least two longitudinal inflatable elements in a desired order.

In a detailed embodiment, the method may include deflating the at least one lateral inflatable element and/or the at least two longitudinal inflatable elements. Deflating the at least one lateral inflatable element and/or the at least two longitudinal inflatable elements may include applying a vacuum to the at least one lateral inflatable element and/or the at least two longitudinal inflatable elements.

In a detailed embodiment, the method may include shielding an anatomical structure other than the target tissue from injury using the spacemaking portion while utilizing a surgical instrument on the target tissue.

In a detailed embodiment, the surgical site may include an oblique sinus and/or the target tissue may include a left atrium.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to surgical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, among other things, surgical instruments and devices for creating surgical working spaces and related methods, and, more specifically, expandable spacemaking devices and related methods. Some example embodiments according to at least some aspects of the present disclosure may be useful in connection with ablation of cardiac tissue, such as to treat cardiac arrhythmias like atrial fibrillation. Some example embodiments according to at least some aspects of the present disclosure may at least partially shield an anatomical structure, such as to reduce the risk of thermal injury to non-targeted anatomical structures during an ablation procedure. The following description begins with an overview of an example embodiment, followed by detailed description of various specific aspects of some example embodiments, and concludes with a description of example methods of using some example embodiments.

Generally, some example spacemaking devices according to at least some aspects of the present disclosure may include one or more expandable structures that can be delivered to surgical sites in a collapsed configuration (e.g., relatively small cross-section). When expanded (e.g., by inflation), the spacemaking devices may create working spaces in which other surgical instruments (e.g., endoscopes, ablation tools, etc.) may be used on target tissues.

Figure 1:
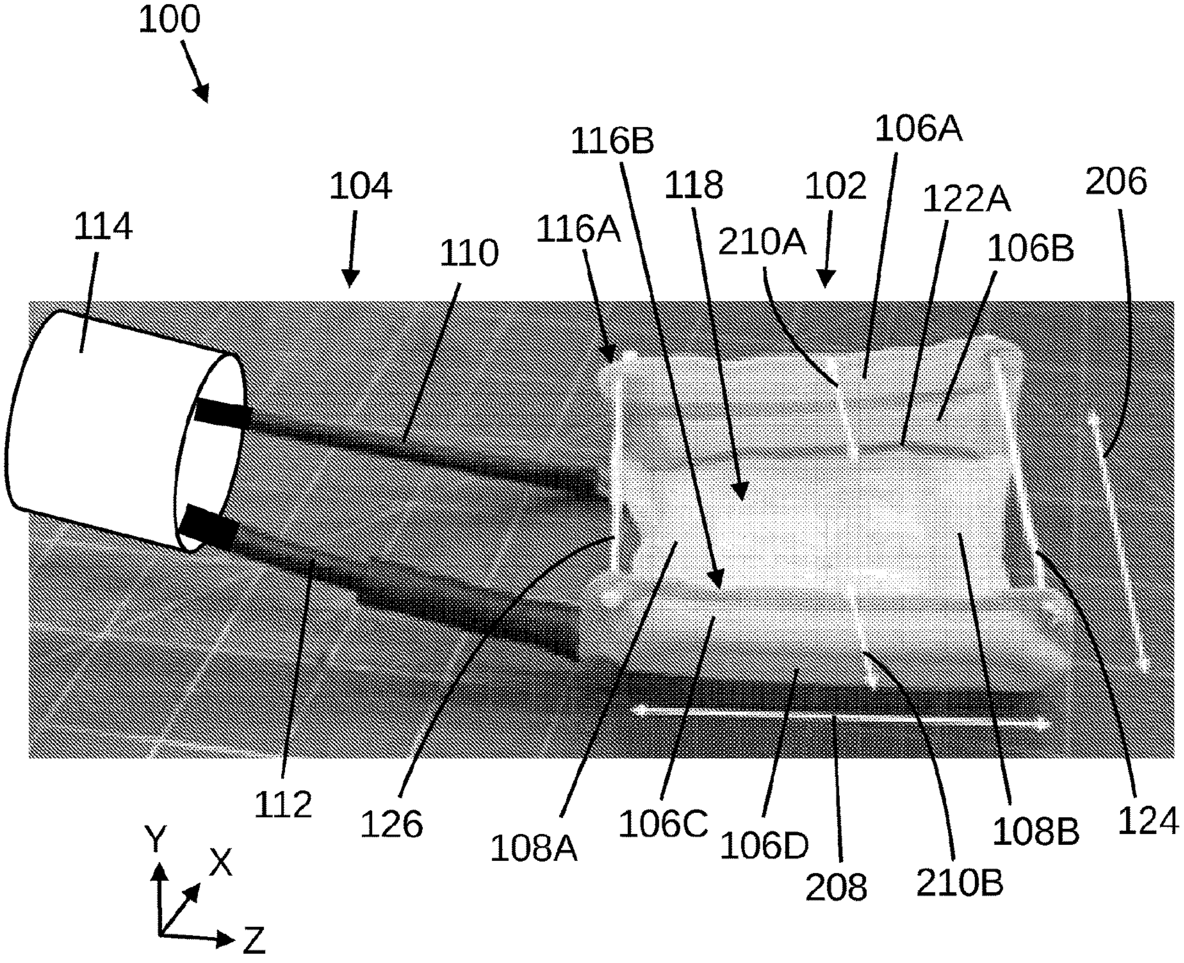
FIG. 1 is a side perspective view of an example spacemaking device in an expanded configuration.
Figure 2:
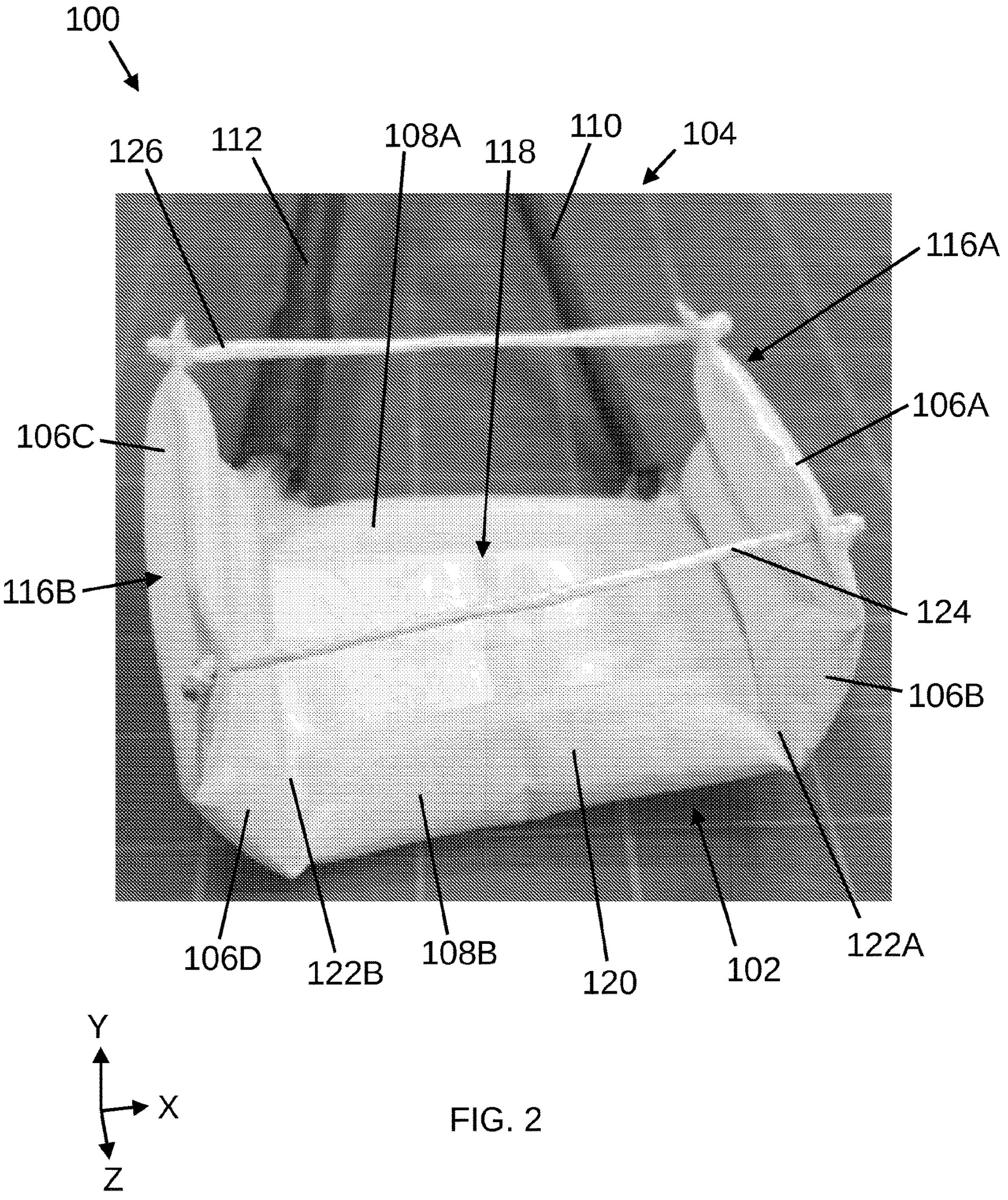
FIG. 2 is an end perspective view of the example spacemaking device of FIG. 1 in the expanded configuration.
Figure 3A:
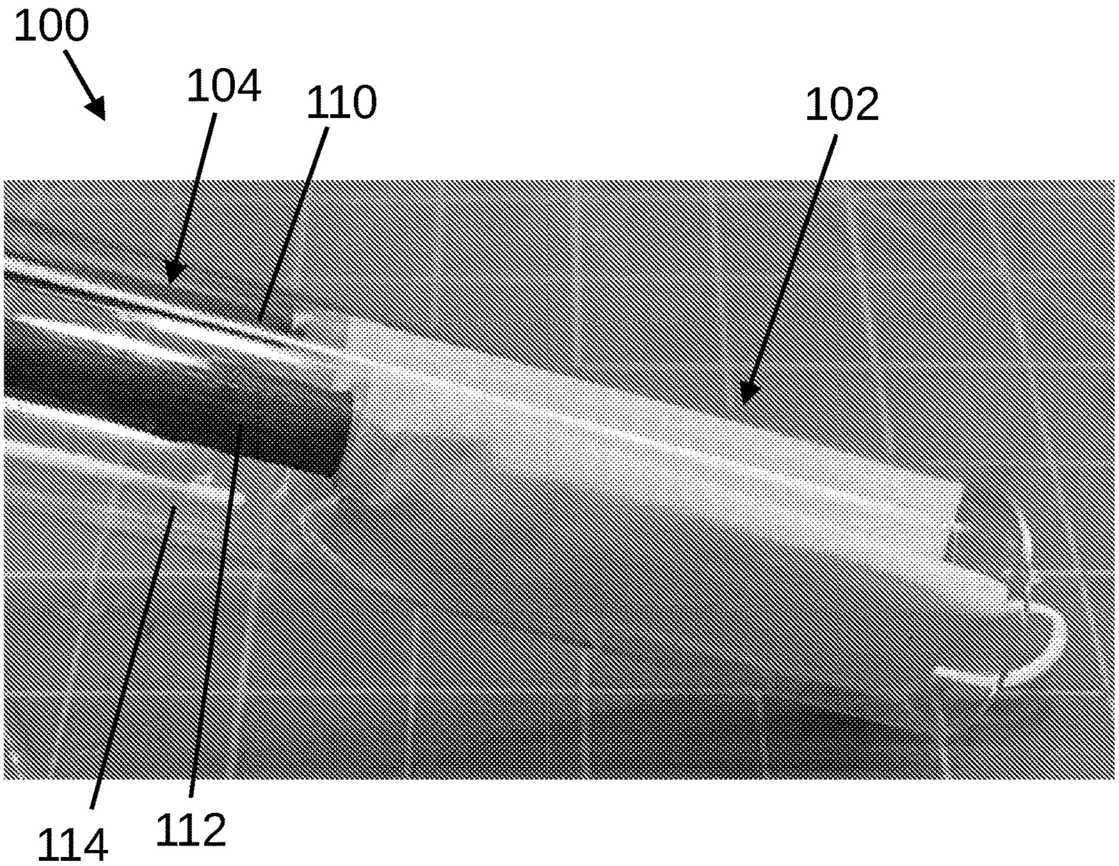
FIG. 3A is a perspective view of the example spacemaking device of FIG. 1 in a collapsed configuration and housed within a sheath.
Figure 3B:
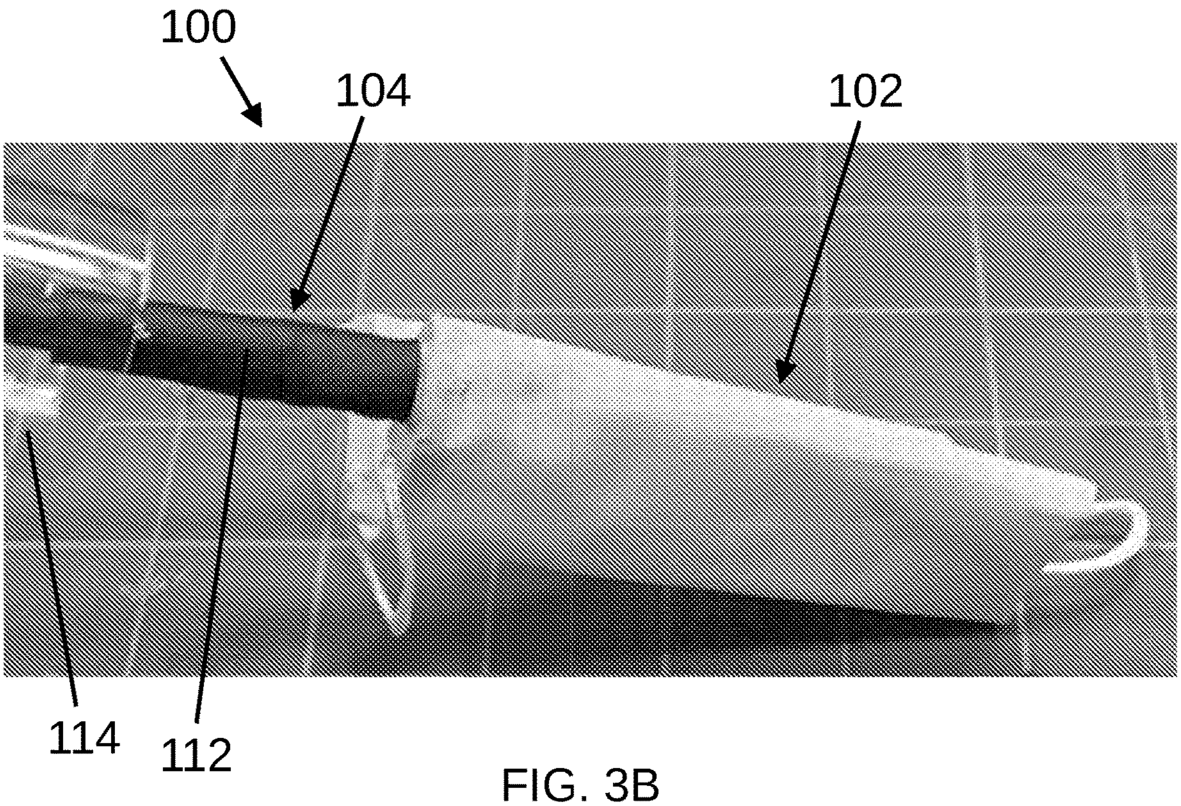
FIG. 3B is a perspective view of the example spacemaking device of FIG. 1 in a collapsed configuration and extended from the sheath.

FIG. 1 is a side perspective view of an example spacemaking device 100 in an expanded configuration, FIG. 2 is an end perspective view of the example spacemaking device 100 in the expanded configuration, FIG. 3A is a perspective view of the example spacemaking device 100 in a collapsed configuration and housed within a sheath, and FIG. 3B is a perspective view of the example spacemaking device 100 in a collapsed configuration and extended from the sheath, all according to at least some aspects of the present disclosure. Referring to FIGS. 1, 2, 3A, and 3B, the example spacemaking device 100 may include an expandable spacemaking portion 102 and/or an elongated connecting portion 104. The spacemaking portion 102 may be disposed distally on the connecting portion 104. As used herein, "distal" may refer to a direction generally away from an operator of a system or device (e.g., a surgeon), such as toward the distant-most end of a device that is inserted into a patient's body. The connecting portion 104 may extend proximally from the spacemaking portion 102 and/or may be manipulated by a user (e.g., surgeon) to position the spacemaking portion 102. As used herein, "proximal" may refer to a direction generally toward an operator of a system or device (e.g., a surgeon), such as away from the distant-most end of a device that is inserted into a patient's body. The spacemaking portion 102 may be expandable and/or collapsible, such as by inflation and/or deflation of one or more longitudinal inflatable elements 106A, 106B, 106C, 106D and/or one or more lateral inflatable elements 108A, 108B. The connecting portion 104 may include one or more tethers 110, 112, which may be operatively coupled to the spacemaking portion 102. For example, the tethers 110, 112 may fluidically couple one or more of the inflatable elements 106A, 106B, 106C, 106D, 108A, 108B to external components. In some example embodiments, the connecting portion 104 may include a sheath 114. The sheath 114 may include one or more internal, generally longitudinal lumens, which may be used to deliver the spacemaking portion 102 and/or other surgical instruments to a surgical site.

Figure 4:
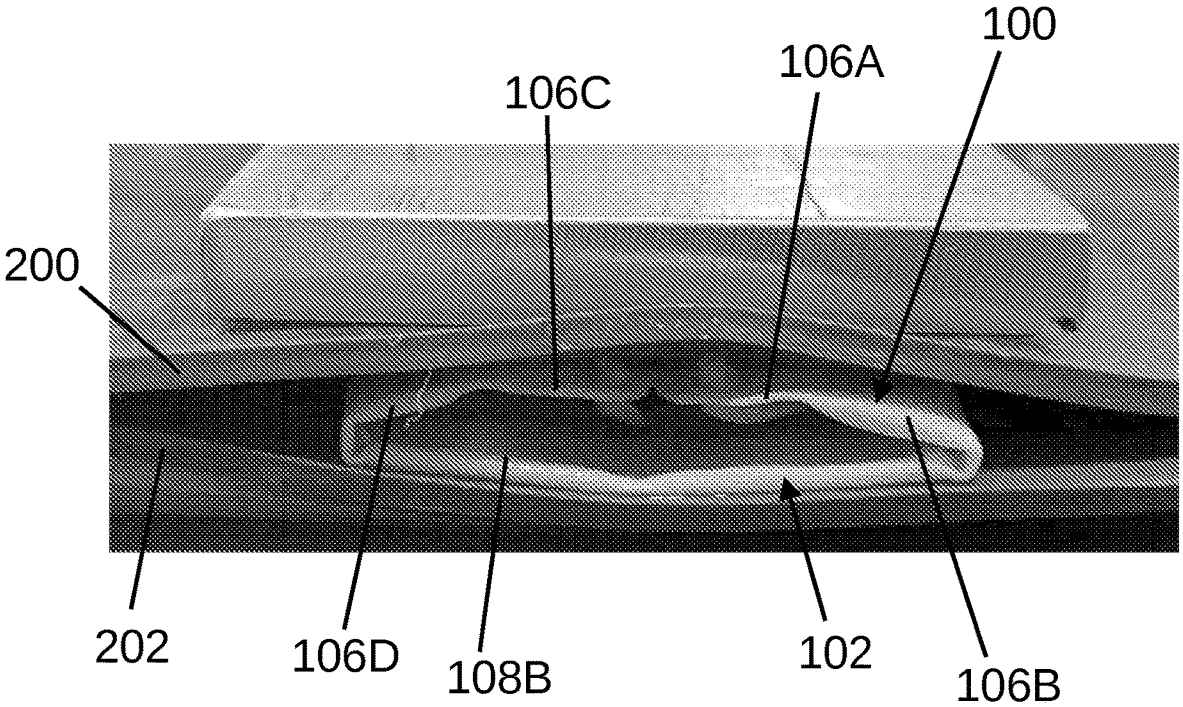
FIG. 4 is an end perspective view of the example spacemaking device of FIG. 1 between two structures 200, 202 and in the collapsed configuration.
Figure 5:
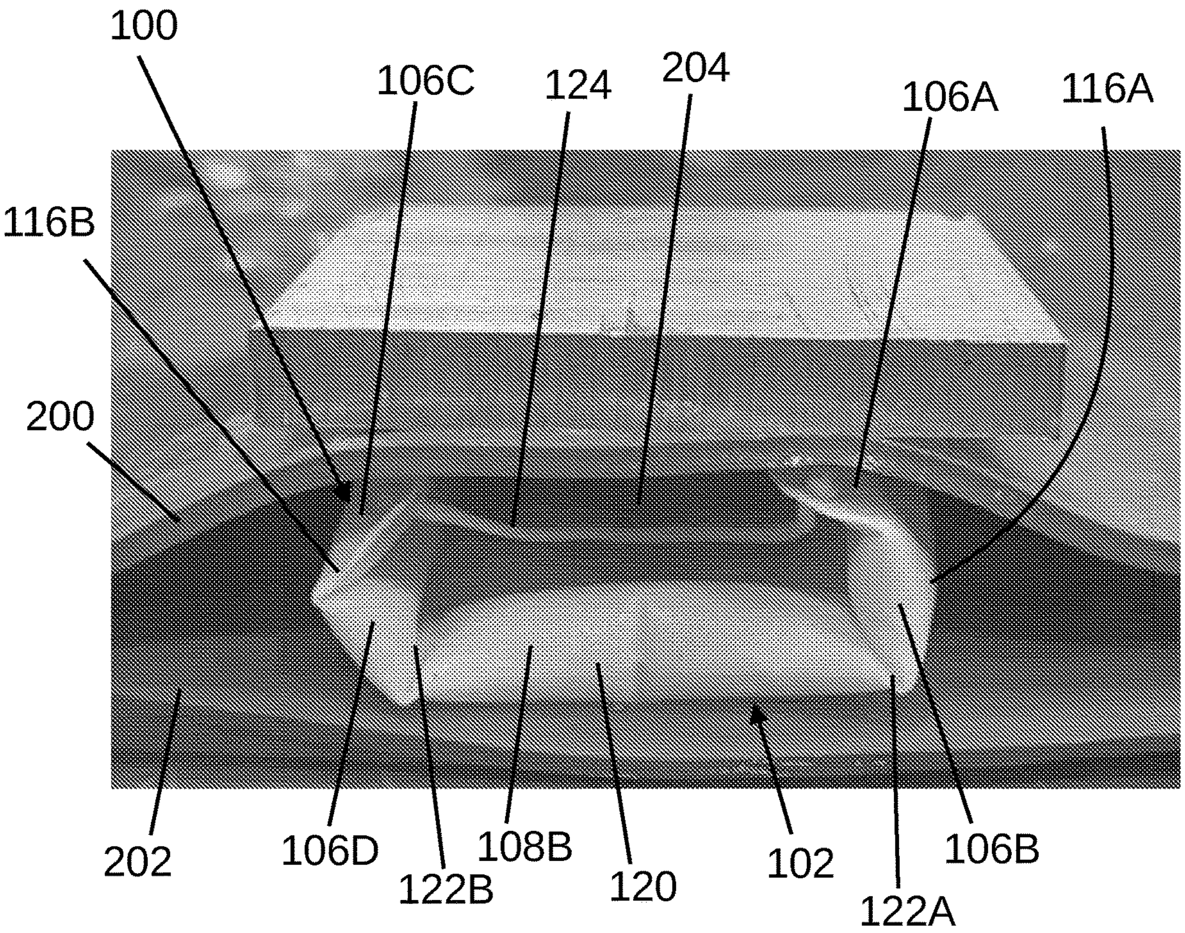
FIG. 5 is an end perspective view of the example spacemaking device of FIG. 1 between the two structures 200, 202 and in the expanded configuration.

FIG. 4 is an end perspective view of the example spacemaking device 100 between two structures 200, 202 in the collapsed configuration and FIG. 5 is an end perspective view of the example spacemaking device 100 between the two structures 200, 202 in the expanded configuration, all according to at least some aspects of the present disclosure. Referring to FIGS. 4 and 5, the first structure 200 and the second structure 202 may form a potential space when no surgical instruments are present therebetween. Positioning of the spacemaking portion 102 of the spacemaking device 100 between the structures 200, 202 may at least partially separate the first structure 200 from the second structure 202. At least partially expanding the spacemaking portion 102 of the spacemaking device 100 (e.g., from the collapsed configuration to the expanded configuration), such as by at least partially inflating one or more of the inflatable elements 106A, 106B, 106C, 106D, 108A, 108B, may further separate the two structures 200, 202, creating a working space 204. In some circumstances, at least partially expanding the spacemaking portion 102 to create the working space 204 may involve applying a separating force greater than the forces holding the structures 200, 202 together. For example, at least partially expanding the spacemaking portion 102 may involve lifting an anatomical structure (e.g., applying a force greater than the weight of the anatomical structure 200 to at least partially raise the anatomical structure 200).

In some example embodiments, one or more of the inflatable elements 106A, 106B, 106C. 106D, 108A, 108B may be at least partially inflated (e.g., expanded) using one or more inflation fluids, such as one or more liquids and/or one or more gasses. Example non-compressible liquids include saline solution, water, and/or dextrose solution. Example compressible gases include room air, nitrogen, carbon dioxide, and/or nitrous oxide. The inflation fluid may be supplied from a syringe, bulb/pump, compressed gas cylinder (e.g., single use or multi use), or other pressurized or pressurizable source of inflation fluid.

In some example embodiments, the pressure of the one or more inflation fluids supplied to the inflatable elements 106A, 106B, 106C, 106D, 108A, 108B (e.g., inflation pressure), may be monitored, controlled, and/or limited. For example, the inflation pressure may be regulated to a target pressure and/or pressure range, such as to obtain a desired degree of expansion of the inflatable elements 106A, 106B, 106C, 106D, 108A, 108B and/or to avoid overinflation of the inflatable elements 106A, 106B, 106C, 106D, 108A, 108B. In some example embodiments, the inflation pressure and/or a related parameter (e.g., force applied to structures 200, 202) may be displayed to a user (e.g., surgeon and/or assistant).

In some example embodiments, one or more of the inflatable elements 106A, 106B, 106C, 106D, 108A, 108B may be at least partially deflated (e.g., collapsed) by draining and/or venting the inflation fluid from the inflatable elements 106A, 106B, 106C, 106D, 108A, 108B, such as to ambient pressure. In some example embodiments, one or more of the inflatable elements 106A, 106B, 106C, 106D, 108A, 108B may be at least partially deflated (e.g., collapsed) by withdrawing the inflation fluid from the inflatable elements 106A, 106B, 106C, 106D, 108A, 108B, such as by applying a vacuum.

Referring to FIG. 1, in some example embodiments, the spacemaking portion 102 of the spacemaking device 100 may be configured expand and/or provide rigidity in one or more directions (e.g., perpendicular axes in X, Y, and Z directions). For example, inflation of one or more inflatable elements (e.g., lateral inflatable elements 108A, 108B) may facilitate expansion and/or rigidity of the spacemaking portion 102 in a generally lateral width direction, indicated by arrow 206 in FIG. 1. Inflation of one or more inflatable elements (e.g., longitudinal inflatable elements 106A, 106B, 106C, 106D) may facilitate expansion and/or rigidity of the spacemaking portion 102 in a generally longitudinal (e.g., proximal-distal) direction, indicated by arrow 208 in FIG. 1. Inflation of one or more inflatable elements (e.g., longitudinal inflatable elements 106A, 106B. 106C, 106D) may facilitate expansion and/or rigidity of the spacemaking portion 102 in a generally lateral height direction, indicated by arrows 210A, 210B in FIG. 1.

In some example embodiments, individual inflatable elements (or individual portions of inflatable elements) may be arranged to respectively facilitate expansion and/or rigidity in each desired direction. That is, an X-direction inflatable element (or portion of an inflatable element) may facilitate expansion and/or rigidity in the X direction, a Y-direction inflatable element (or portion of an inflatable element) may facilitate expansion and/or rigidity in the Y direction, and/or a Z-direction inflatable element (or portion of an inflatable element) may facilitate expansion and/or rigidity in the Z direction.

In some example embodiments, the spacemaking portion 102 may be configured so that one or more of the inflatable elements 106A, 106B, 106C, 106D, 108A, 108B may facilitate expansion and/or rigidity in two or more directions. For example, in the spacemaking portion 102 shown in FIGS. 1-5, the longitudinal inflatable elements 106A, 106B may be disposed in an upstanding first lateral portion 116A and/or the longitudinal inflatable elements 106C, 106D may be disposed in an upstanding second lateral portion 116B. The lateral portions 116A, 116B may be configured to extend generally laterally vertically (e.g., generally orthogonally) relative to a lateral base portion 118, which may include the lateral inflatable elements 108A, 108B. As used herein, terms such as "vertically" are to be understood as relative terms in the context of the description herein and are not to be understood as limited to a particular orientation with respect to the Earth.

In some example embodiments, one or more upstanding portions (e.g., lateral portions 116A. 116B) may be formed by folding a spacemaking portion body 120 along one or more creases (e.g., fold lines) 122A, 122B, which may be respectively associated with the lateral portions 116A, 116B. While the example embodiment shown in FIGS. 1-5 includes generally longitudinal (e.g., proximal-distal) creases 122A, 122B at least partially defining the lateral portions 116A, 116B, alternative example embodiments may include one or more creases oriented in any direction to at least partially define upstanding portions in other orientations.

In some example embodiments, one or more upstanding portions (e.g., lateral portions 116A, 116B) may be positioned in a desired orientation (e.g., a generally upstanding manner relative to the lateral base portion 118) by one or more positioning elements. For example, the spacemaking portion 102 may include one or more tension elements 124, 126 operatively coupled between the lateral portions 116A, 116B. For example, the distal lateral tension element 124 may extend between distal aspects of the lateral portions 116A, 116B and/or the proximal lateral tension element 126 may extend between proximal aspects of the lateral portions 116A. 116B. Generally, the tension elements 124, 126 may cause the spacemaking portion body 120 to generally form a C-shape when the inflatable elements 106A, 106B, 106C, 106D, 108A, 108B are inflated, as seen in FIGS. 2 and 5, for example. Generally, the open portion of the C-shape, which may be occupied by one or more of the tension elements 124, 126, may create an open space providing access to the adjacent tissue 200 from within the working space 204. In some example embodiments, the tension elements 124, 126 may be constructed from generally elastic and/or generally inelastic materials. As used herein, "elastic" may refer to materials that substantially elastically deform under expected loads during the intended use of the device. As used herein, "inelastic" may refer to materials that do not substantially elastically deform under expected loads during the intended use of the device. Referring to FIG. 5, the spacemaking portion 102 may form the generally open working space 204 generally between the upstanding, lateral edges of the lateral portions 116A, 116B.

Referring to FIGS. 1, 2, and 5, in some example embodiments, at least a portion of the spacemaking portion body 120 may be configured to shield nearby anatomical structures. For example, the base portion 118 of the spacemaking portion body 120 may be substantially continuous (e.g., substantially without openings extending laterally therethrough). Accordingly, the second structure 202 may be at least partially shielded by the base portion 118 from a surgical procedure performed within the working space 204. That is, the base portion 118 may physically interpose the working space 204 and the second structure 202. For example, if an ablation procedure is performed within the working space, the base portion 118 may at least partially shield the second structure 202 from thermal injury due to the ablation procedure.

In some example embodiments, the spacemaking portion body 120 may be constructed from and/or covered with one or more materials configured to provide a desired frictional engagement with the first structure 200 and/or the second structure 202. For example, at least a portion of the spacemaking portion body 120 may be constructed from and/or covered by a relatively high-friction fabric having a surface roughness selected to provide a desired frictional engagement to prevent movement of the spacemaking portion body 120 relative to one or both of the structures 200, 202. In some example embodiments, at least a portion of the spacemaking portion body 120 may be constructed from and/or covered with a relatively low-friction material to facilitate movement of the spacemaking portion 102 relative to adjacent structures, such as one or both of the structures 200, 202 and/or an interior lumen of the sheath 114.

In some example embodiments, at least a portion of the spacemaking portion 102 may be constructed from one or more generally opaque and/or generally translucent materials of one or more desired colors. In some example embodiments at least a portion of the spacemaking portion 102 may be constructed from one or more generally transparent (e.g., clear) materials, which may facilitate visualization of structures and/or devices through the generally transparent portion(s).

In some example embodiments, at least a portion of the spacemaking portion 102 may be constructed from one or more generally compliant materials. As used herein, "compliant" may refer to a material that generally readily conforms to a surface of an abutting structure. In some example embodiments, at least a portion of the spacemaking portion 102 may be constructed from one or more generally non-compliant materials. As used herein, "non-compliant" may refer to a material that generally maintains its shape without readily conforming to a surface of an abutting structure. In some example embodiments, the spacemaking portion 102 may be constructed from both compliant and non-compliant materials, which may be arranged to achieve desired expanded/collapsed configurations, for example.

In some example embodiments, one or more portions of the spacemaking portion 102 may be constructed to provide more or less force or expansion in certain directions. For example, one or more portions of the spacemaking portion 102 may have a wall thickness that differs from a wall thickness in another portion of the spacemaking portion 102. In some example embodiments, at least a portion of the spacemaking portion 102 may be constructed with oriented fibers arranged to provide selective expansion in one or more desired directions. For example, the expansion may be greater in one direction than another direction.

In some example embodiments, one or more portions of the spacemaking portion 102 may be constructed in the manner of an expandable bellows. For example, a material may include a plurality of back-and-forth folds configured generally to collapse and stack together when deflated and/or to straighten and/or unfold when inflated. Such a configuration may facilitate expansion in a desired direction, for example.

In some example embodiments, one or more of the inflatable elements 106A, 106B, 106C, 106D, 108A, 108B may be fluidically isolated from one or more other inflatable elements 106A, 106B, 106C, 106D, 108A, 108B. Such a configuration may facilitate selective inflation and/or deflation, such as inflation and/or deflation of only some, but not all, of the inflatable elements 106A, 106B, 106C, 106D, 108A, 108B. Such a configuration may facilitate sequential inflation and/or deflation, such as inflation and/or deflation of two or more inflatable elements 106A, 106B, 106C. 106D, 108A, 108B in a desired sequence. That is, one or more of the inflatable elements 106A, 106B, 106C, 106D, 108A, 108B may be inflated and/or deflated before or after other inflatable elements 106A, 106B, 106C, 106D, 108A, 108B are inflated and/or deflated. Such a configuration may prevent complete deflation of the spacemaking portion 102 (e.g., deflation of all of the inflatable elements 106A, 106B, 106C. 106D, 108A, 108B comprising the spacemaking portion 102) if the integrity of one or more of the inflatable elements 106A, 106B, 106C, 106D, 108A, 108B is lost, such as due to failure or puncture.

In some example embodiments, the connecting portion 104 may be used to apply forces to the spacemaking portion 102. For example, externally applied tension, compression, and/or torsion may be transmitted to the spacemaking portion 102 via the tethers 110, 112 and/or the sheath 114. In some example embodiments, the connecting portion 104 (e.g., tethers 110, 112 and/or sheath 114) may be used to prevent movement of the spacemaking portion 102. For example, the connecting portion 104 may be externally secured to anchor the spacemaking portion 102 in a desired position proximate a surgical site.

In some example embodiments, the spacemaking device 100 may be steerable. For example, the connecting portion 104 may include one or more steering elements configured to steer one or more of the tethers 110, 112, the sheath 114, and/or the spacemaking portion 102. In some example embodiments, the steering elements may include steering tethers which may be tensioned proximally to direct a distal portion of the spacemaking device 100. In some example embodiments, the connecting portion 104 may include integrated steering functionality, generally similar to a steerable sheath.

Example methods of creating a working space using example spacemaking devices according to at least some aspects of the present disclosure are described below. The following description focuses on use of the example spacemaking device 100 described above; however, at least some of the operations may also be applicable to other spacemaking devices according to at least some aspects of the present disclosure. Further, the example methods described below focus on the use of example spacemaking devices in the context of ablation of portions of the left atrium, such as in connection with treatment of atrial fibrillation; however, example methods according to at least some aspects of the present disclosure may be utilized in connection with surgical procedures performed at other anatomical locations and/or for other purposes.

Figure 6:
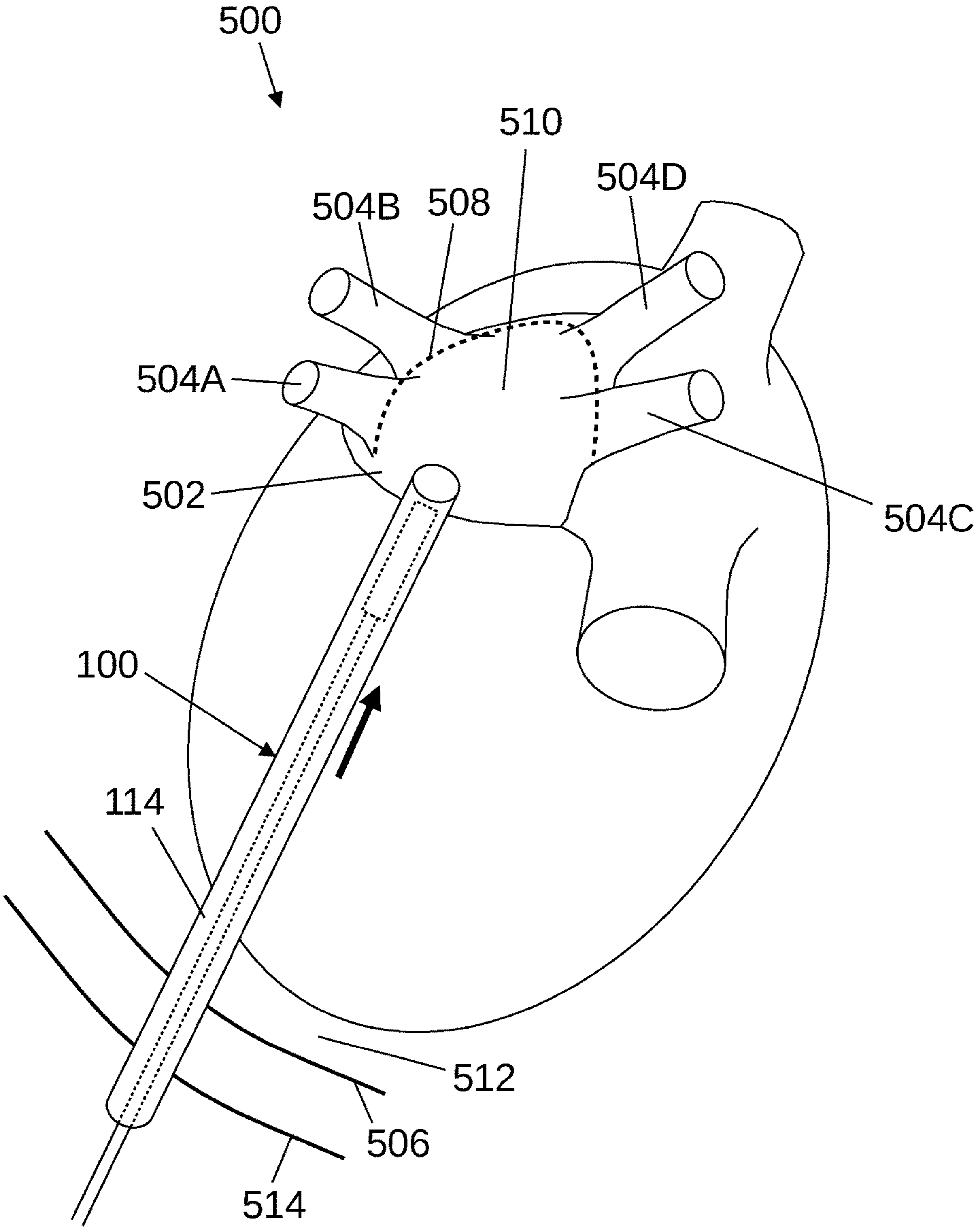
FIG. 6 is a simplified posterior perspective view of a heart illustrating an example method of using an example spacemaking device.

FIGS. 6-11 are simplified posterior (rear) perspective views of a heart 500 illustrating example methods of using an example spacemaking device 100, all according to at least some aspects of the present disclosure. Referring to FIG. 6, the posterior left atrium 502 of the heart 500 may be an anatomic ablation target for the treatment of atrial fibrillation. The left atrium 502 is located generally on the posterior (rear) surface of the heart 500 and receives blood from the lungs through the pulmonary veins 504A, 504B, 504C, 504D. The pericardium 506, the sac containing the heart 500, is attached to the surface of the heart 500 at pericardial reflections 508 near the pulmonary veins 504A, 504B, 504C, 504D. These pericardial reflections 508, in connection with the pulmonary veins 504A, 504B, 504C, 504D, define a potential space on the posterior side of the left atrium 502 referred to as the oblique sinus 510. Some surgical procedures, such as ablation of portions of the left atrium 502, may involve operations performed within the oblique sinus 510.

Some example methods of creating a surgical working space may include directing a spacemaking device 100 to a surgical site (e.g., the oblique sinus 510), which may be proximate a target tissue (e.g., a left atrium). For example, a surgeon may obtain access into the pericardial space 512 (e.g., the interior of the pericardium 506). This may be accomplished using surgical and/or percutaneous methods through the skin 514 and intervening anatomical structures, such as via a sub-xiphoid and/or intercostal approach. As illustrated in FIG. 6, in some example embodiments, the spacemaking device 100 (e.g., the sheath 114) may be advanced into the pericardial space 512, such as into the oblique sinus 510. In other example embodiments, a delivery sheath separate from the spacemaking device 100 may be advanced into the pericardial space 512 (e.g., oblique sinus 510), and the spacemaking device 100 may be delivered via the separate delivery sheath. The spacemaking device 100 and/or delivery sheath may be guided using endoscopy and/or fluoroscopy, for example.

Figure 7:
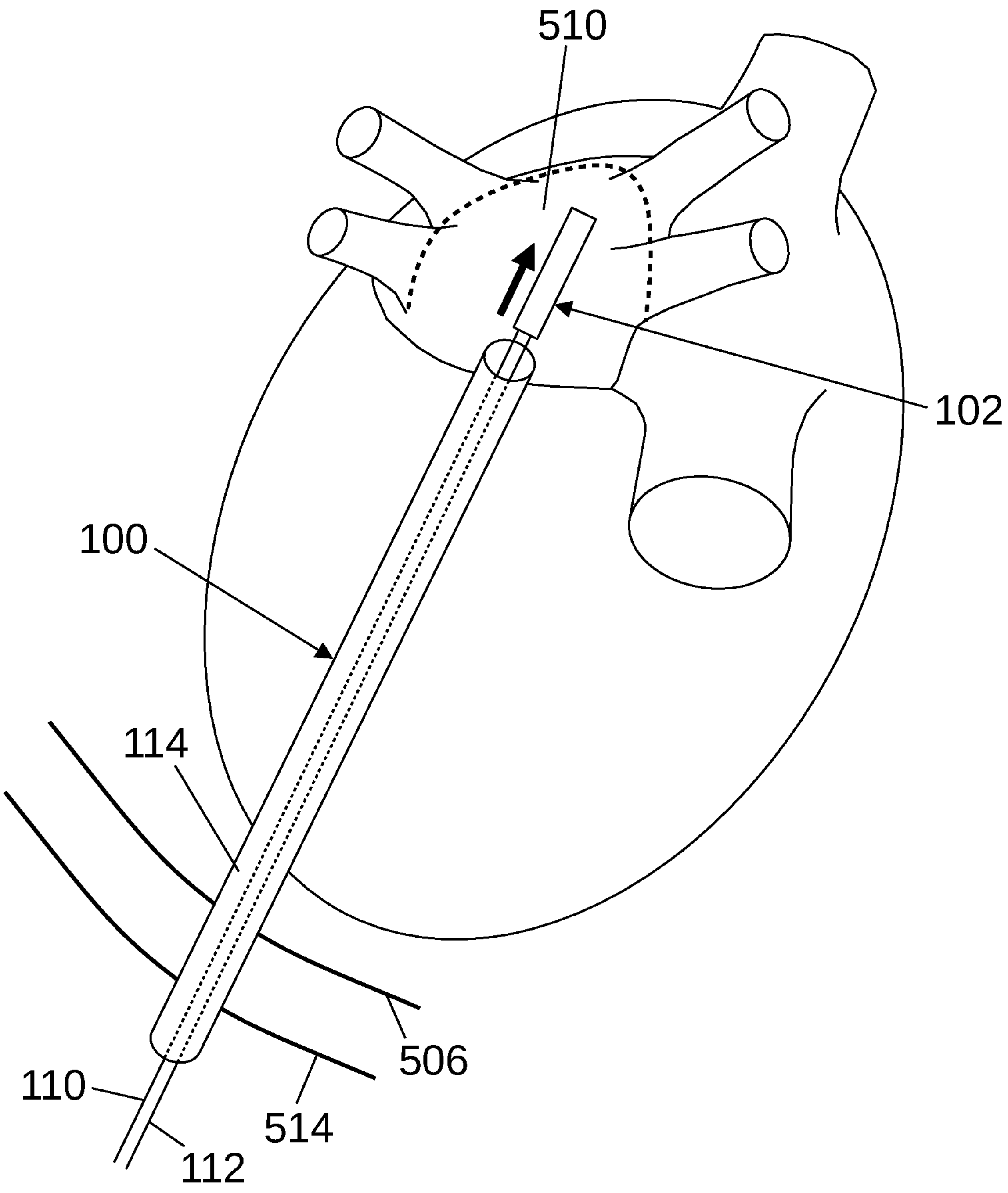
FIG. 7 is a simplified posterior perspective view of a heart illustrating an example method of using an example spacemaking device.

Referring to FIG. 7, the spacemaking portion 102 of the spacemaking device 100 may be deployed, such as into the oblique sinus 510. In some example embodiments, the spacemaking portion 102 may be at least partially contained within the sheath 114 while the sheath is advanced into the pericardial space 512 through the pericardium 506. Then, the spacemaking portion 102 may be unsheathed from the sheath 114 to deploy the spacemaking portion 102 into the oblique sinus 510. In other example embodiments, the spacemaking device 100 may be inserted through a separate delivery sheath, and the spacemaking portion 102 may be extended distally beyond the distal end of the separate delivery sheath and into the oblique sinus 510. Proximal components of the spacemaking device 100, such as a proximal portion of the sheath and/or proximal portions of the tethers 110, 112, may remain outside of the skin 514.

Figure 8:
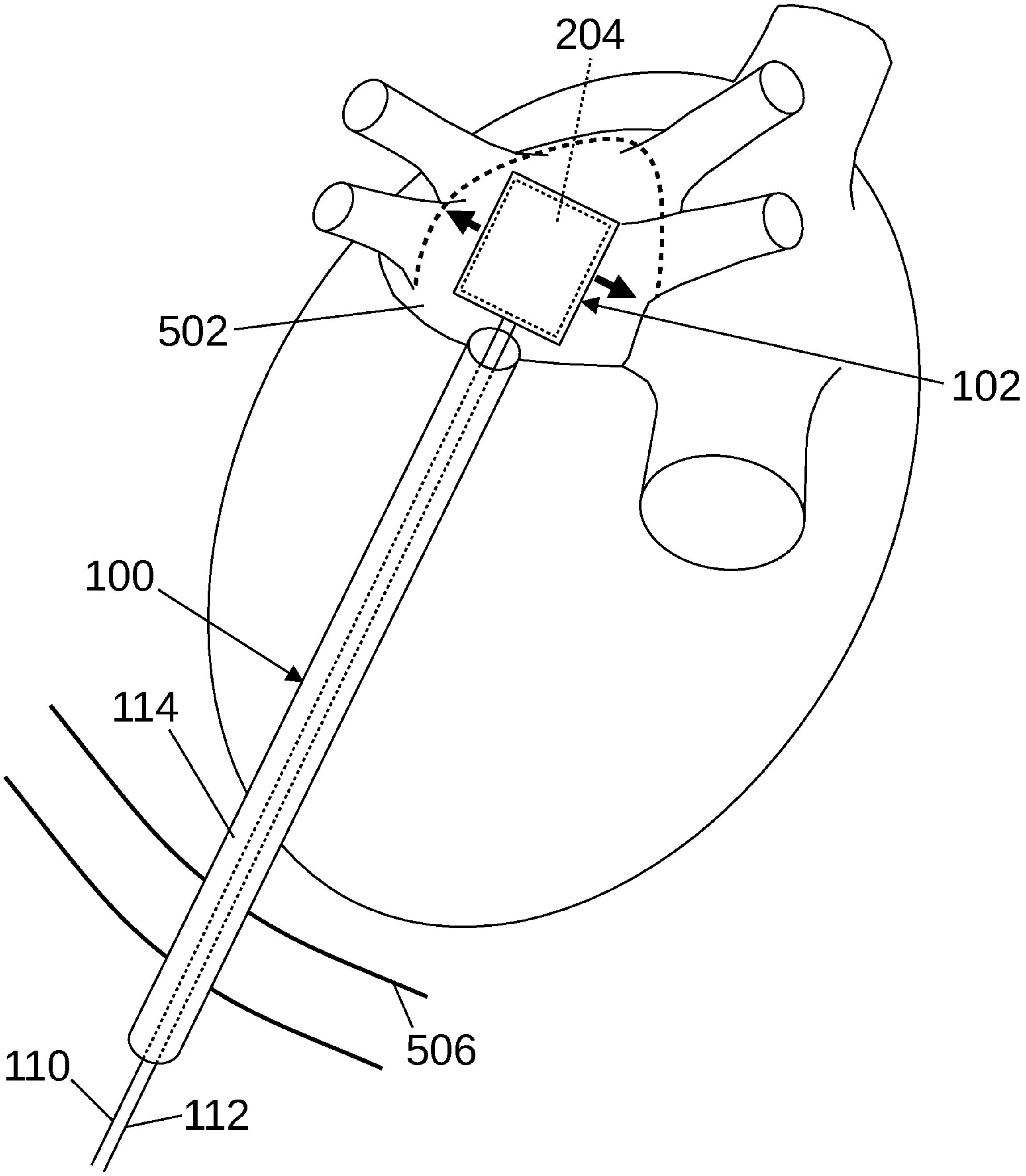
FIG. 8 is a simplified posterior perspective view of a heart illustrating an example method of using an example spacemaking device.

Referring to FIG. 8, the spacemaking portion 102 of the spacemaking device 100 may be at least partially expanded. For example, one or more of the inflatable elements 106A, 106B, 106C, 106D, 108A, 108B (FIGS. 1 and 2) may be inflated, such as by suppling pressurized inflation fluid via one or more of the tethers 110, 112. Expansion of the spacemaking portion 102 may separate the pericardium 506 (e.g., corresponding to the structure 202 in FIGS. 4 and 5) from the surface of the left atrium 502 (e.g., corresponding to the structure 200 in FIGS. 4 and 5), creating the working space 204 (FIGS. 4, 5, and 8). In some example embodiments, expanding the spacemaking portion 102 to create the working space 204 in the oblique sinus 510 may involve at least partially lifting the heart 500. In some example embodiments, the spacemaking portion 102 may be configured to expand in a controlled manner, such as by unfurling, unrolling, and/or unfolding.

Figure 9:
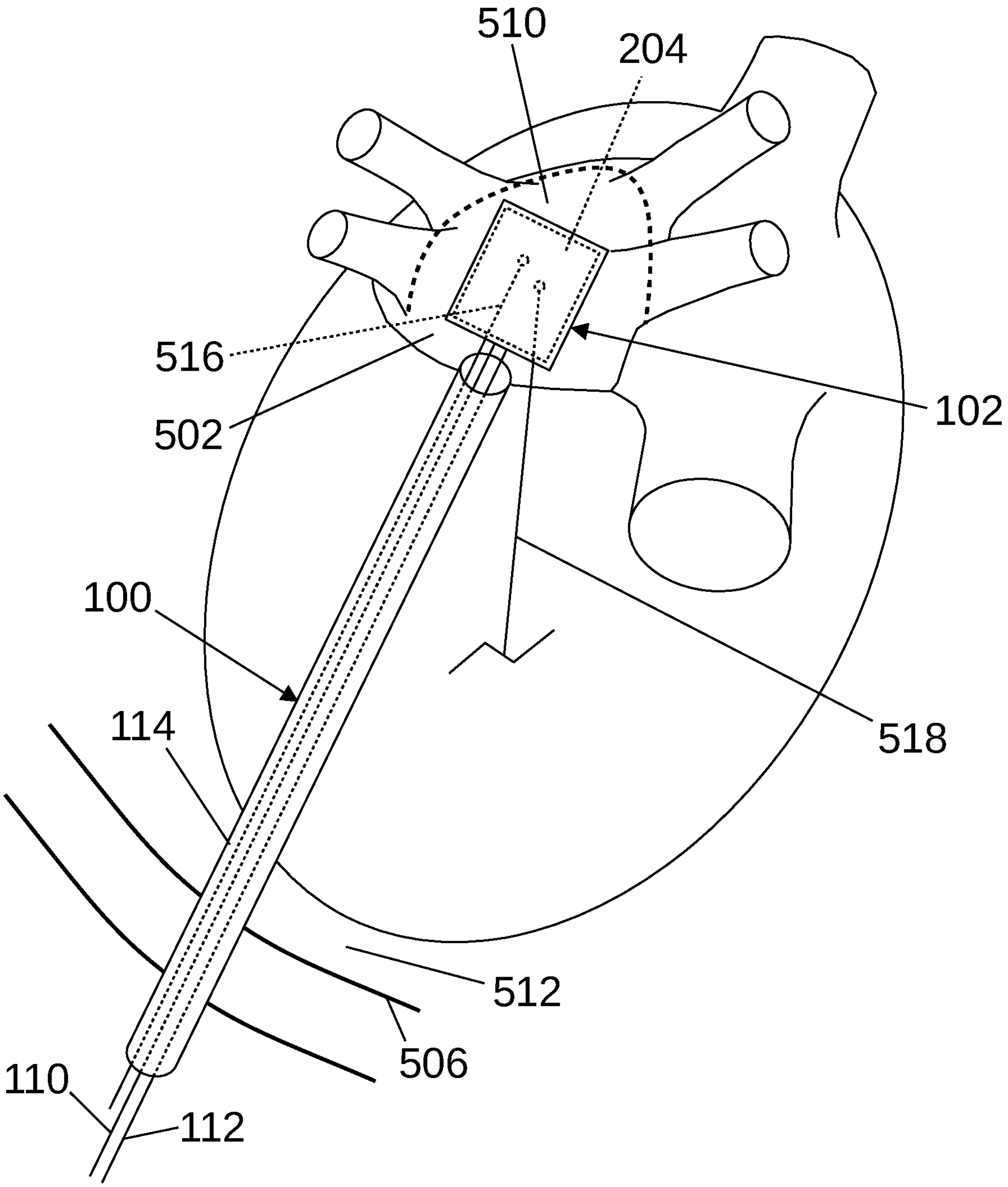
FIG. 9 is a simplified posterior perspective view of a heart illustrating an example method of using an example spacemaking device.

Referring to FIG. 9, after the spacemaking portion 102 is at least partially expanded, one or more surgical instruments 516, 518 may be delivered into the working space 204. For example, one or more visualization instruments (e.g., endoscopes) and/or one or more ablation instruments (e.g., radiofrequency ablation instruments) may be positioned and/or utilized in and/or near the working space 204. Generally, the entry from the skin incision into the pericardial space 512 may cross multiple tissue planes and/or the path from the incision to the oblique sinus 510 may be three dimensional. The spacemaking device 100 may provide a track that other surgical instruments may follow to the oblique sinus 510. In some example, embodiments, one or more surgical instruments 516 may be delivered to the working space 204 via the sheath 114 of the spacemaking device 100. In some example embodiments, one or more surgical instruments 518 may be delivered to the working space 204 separately from the spacemaking device 100, such as adjacent to the spacemaking device via the same access path and/or via another access path.

In some example embodiments, the surgical instruments 516, 518 may be used to visualize anatomical landmarks, guide ablation tools, ablate target tissues, etc. as required to accomplish the purpose of the surgical procedure. For example, an endoscope may be utilized to visualize anatomical variations of the oblique sinus boundaries, which may vary substantially from patient to patient. Creation of the working space 204 and/or facilitating visualization of the anatomical landmarks may assist in standardizing some aspects of surgical procedures, such as ablation lesion placement, regardless of patient anatomical variations and user (e.g., surgeon) technique.

In some example embodiments, at least a portion of the spacemaking portion 102 may act as a shield to reduce the risk of injury to tissues near the surgical site. For example, the esophagus lies immediately posterior to the oblique sinus 510 and may be injured when ablation is performed in the oblique sinus 510. In some example embodiments, the base portion 118 (FIGS. 1 and 2) of the spacemaking portion 102 may protect the esophagus from injury when thermal ablation is performed on the left atrium 502. After the operations at the surgical site within the working space 204 are complete, the surgical instruments 516, 518 may be withdrawn.

Figure 10:
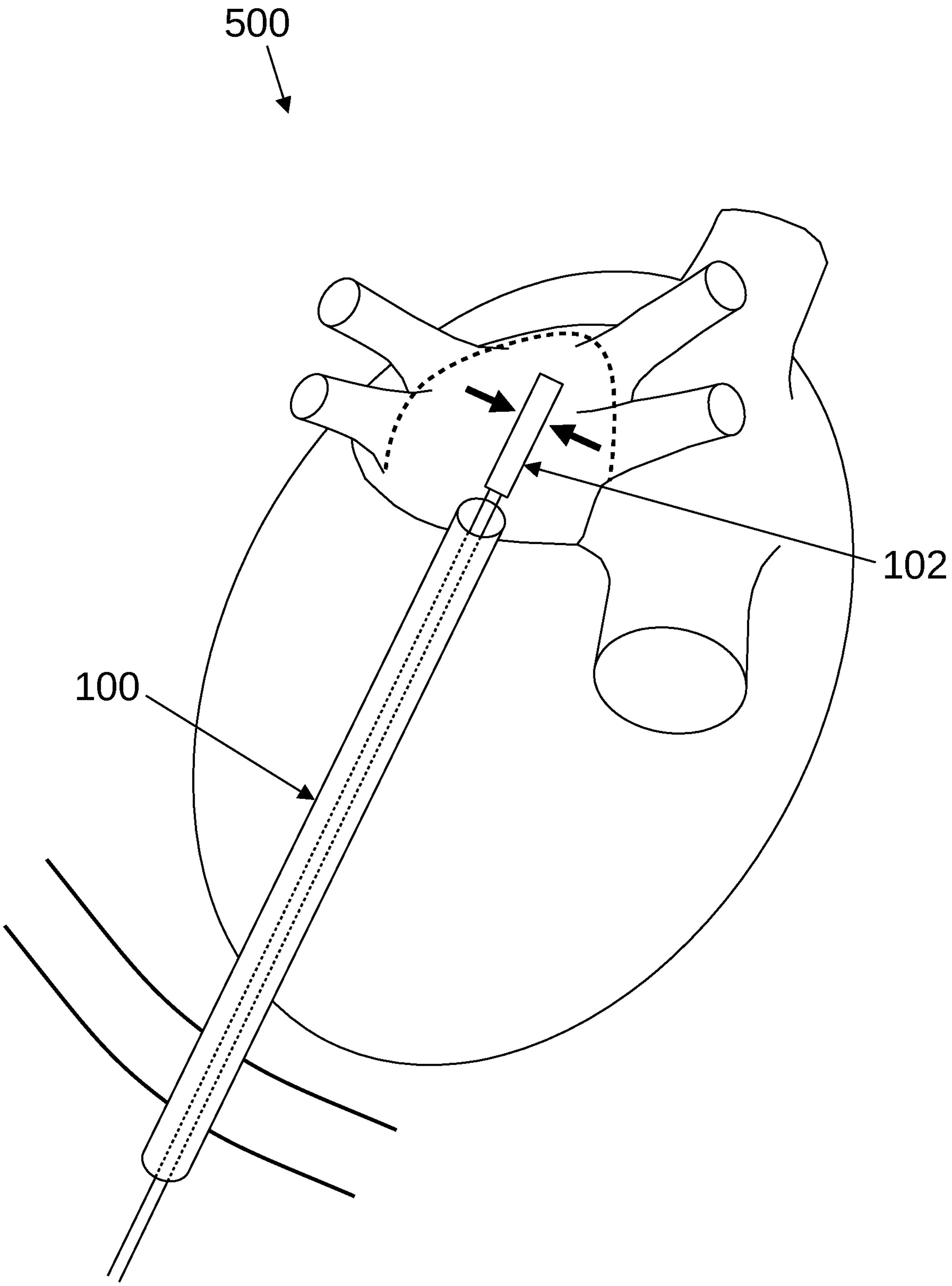
FIG. 10 is a simplified posterior perspective view of a heart illustrating an example method of using an example spacemaking device.

Referring to FIG. 10, the spacemaking portion 102 of the spacemaking device 100 may be at least partially collapsed, such as by deflating one or more of the inflatable elements 106A, 106B. 106C, 106D, 108A, 108B (FIGS. 1 and 2). In some example embodiments, the spacemaking portion 102 may be configured to collapse in a controlled manner, such as by furling, rolling, and/or folding.

Figure 11:
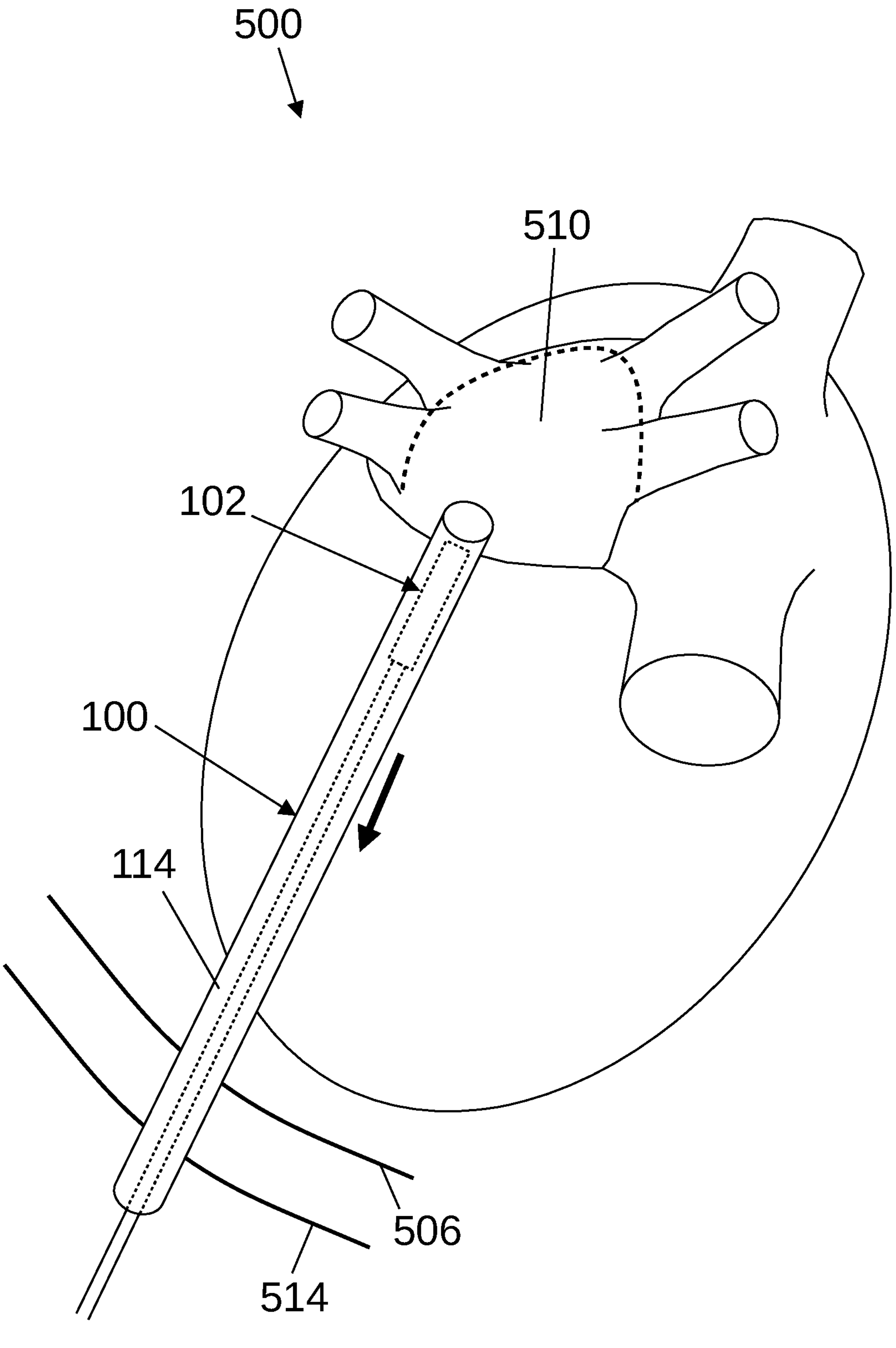
FIG. 11 is a simplified posterior perspective view of a heart illustrating an example method of using an example spacemaking device; all in accordance with at least some aspects of the present disclosure.

Referring to FIG. 11, after the spacemaking portion 102 of the spacemaking device 100 has been at least partially collapsed, the spacemaking device 100 may be withdrawn from the oblique sinus 510. In some example embodiments, the spacemaking portion 102 may be withdrawn at least partially within the sheath 114, and then the sheath 114 may be withdrawn from the oblique sinus 510. The spacemaking device 100 may be withdrawn from the patient's body (e.g., via the pericardium 506 and/or the skin 514).

Example methods of manufacturing spacemaking devices and components thereof may include operations associated with acquiring, producing, and assembling various parts, elements, components, and systems described herein.

Although some example embodiments have been described above in connection with realizing a working space from a potential space, some example embodiments may be used to dilate (e.g., make wider or larger) anatomical openings and/or to develop tissue planes, such as by separating adjacent, at least partially connected tissue layers.

Unless specifically indicated, it will be understood that the description of the structure, function, and/or methodology with respect to any illustrative embodiment herein may apply to any other illustrative embodiments. More generally, it is within the scope of the present disclosure to utilize any one or more features of any one or more example embodiments described herein in connection with any other one or more features of any other one or more other example embodiments described herein. Accordingly, any combination of any of the features or embodiments described herein is within the scope of this disclosure.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope of the disclosure. Likewise, it is to be understood that it is not necessary to meet any or all of the identified advantages or objects disclosed herein in order to fall within the scope of the disclosure, since inherent and/or unforeseen advantages may exist even though they may not have been explicitly discussed herein.

What is claimed is:

1. A surgical spacemaking device, comprising:
an elongated connecting portion; and
an expandable spacemaking portion disposed distally on the connecting portion, the spacemaking portion comprising
an expandable base portion,
an expandable first lateral portion coupled to the lateral base portion, and
an expandable second lateral portion coupled to the lateral base portion;
wherein, when expanded, a first exterior surface of the first lateral portion faces a second exterior surface of the second lateral portion;
wherein, when expanded, the first and second exterior surfaces cooperate with an exterior surface of the base portion to define a working space;
wherein a tension line couples the first lateral portion to the second lateral portion; wherein the tension line comprises a distal tension line extending between distal aspects of the first lateral portion and the second lateral portion.

2. The surgical spacemaking device of claim 1, wherein, when expanded, the base portion, the first lateral portion, and the second lateral portion generally form a C-shape.

3. The surgical spacemaking device of claim 1, wherein the tension line comprises a proximal tension line extending between proximal aspects of the first lateral portion and the second lateral portion.

4. The surgical spacemaking device of claim 1, wherein the tension line is generally inelastic.

5. The surgical spacemaking device of claim 1, wherein the base portion comprises a bladder.

6. The surgical spacemaking device of claim 1,
wherein the first lateral portion comprises a first bladder; and
wherein the second lateral portion comprises a second bladder.

7. The surgical spacemaking device of claim 1,
wherein the base portion and the first lateral portion are interposed by a first fold line; and
wherein the base portion and the second lateral portion are interposed by a second fold line.

8. The surgical spacemaking device of claim 1,
wherein the base portion, the first lateral portion, and the second lateral portion comprise a bladder in fluid communication with the elongated connecting portion.

9. A surgical spacemaking device, comprising:
an elongated connecting portion; and
an expandable spacemaking portion disposed distally on the connecting portion, the spacemaking portion comprising
an expandable base portion,
an expandable first lateral portion coupled to the base portion, and
an expandable second lateral portion coupled to the base portion;
wherein, when expanded, a first exterior surface of the first lateral portion faces a second exterior surface of the second lateral portion;
wherein, when expanded, the first and second exterior surfaces cooperate with an exterior surface of the base portion to define a working space;
wherein a tension line couples the first lateral portion to the second lateral portion;
wherein the tension line is generally elastic.

10. A surgical spacemaking device, comprising:
an elongated connecting portion; and
an expandable spacemaking portion disposed distally on the connecting portion, the spacemaking portion comprising
an expandable base portion,
an expandable first lateral portion coupled to the lateral base portion, and
an expandable second lateral portion coupled to the lateral base portion;
wherein, when expanded, a first exterior surface of the first lateral portion faces a second exterior surface of the second lateral portion;
wherein, when expanded, the first and second exterior surfaces cooperate with an exterior surface of the base portion to define a working space;
wherein a tension line couples the first lateral portion to the second lateral portion;
wherein the connecting portion comprises a tether operatively coupled to the spacemaking portion;
wherein the connecting portion comprises a sheath;
wherein the tether extends through the sheath.

11. The surgical spacemaking device of claim 10, wherein the tether is fluidically coupled to at least one of the base portion, the first lateral portion, and the second lateral portion.

12. The surgical spacemaking device of claim 10, wherein the sheath is configured to receive at least one of an endoscope and an ablation device therethrough.

13. A method of creating a surgical working space, the method comprising:
advancing a spacemaking device within a sheath to a surgical site proximate a target tissue;
distally unsheathing a spacemaking portion of the spacemaking device from the sheath;
expanding the spacemaking portion of the spacemaking device to create a working space; and
advancing at least one of an endoscope and an ablation instrument through the sheath to the working space;
wherein expanding the spacemaking portion comprises inflating at least two lateral bladders coupled to a base, the at least two lateral bladders being coupled by at least one tension line.

14. The method of claim 13, wherein expanding the spacemaking portion comprises expanding the spacemaking portion so that exterior surfaces of the at least two lateral bladders and the base generally form a C-shape with the working space at least partially therein.

15. The method of claim 13, wherein expanding the spacemaking portion comprises at least one of inflating the base after inflating the at least two lateral bladders, inflating the base while inflating the at least two lateral bladders, and inflating the base before inflating the at least two lateral bladders.

16. The method of claim 13, further comprising deflating the at least two lateral bladders.

17. The method of claim 16, wherein deflating the at least two lateral bladders comprises applying a vacuum to the at least two lateral bladders.

18. The method of claim 13, further comprising shielding an anatomical structure other than the target tissue from injury using the spacemaking portion while utilizing a surgical instrument on the target tissue.

19. A method of creating a surgical working space, the method comprising:

advancing a spacemaking device to a surgical site comprising an oblique sinus, proximate a left atrium; and expanding a spacemaking portion of the spacemaking device to create a working space;

wherein expanding the spacemaking portion comprises inflating at least two lateral inflatable elements coupled to a base element, the at least two lateral inflatable elements being coupled by at least one tension line.

* * * * *